United States Patent
Foley et al.

(10) Patent No.: US 7,169,152 B2
(45) Date of Patent: Jan. 30, 2007

(54) METHODS AND INSTRUMENTS FOR INTERBODY SURGICAL TECHNIQUES

(75) Inventors: Kevin T. Foley, Germantown, TN (US); Jeffrey D. Moore, Horn Lake, MS (US); Bradley T. Estes, Memphis, TN (US); Mingyan Liu, Bourge la Reine (FR); Loic Josse, Palaja (FR)

(73) Assignee: SDGI Holdings, Inc., Wilmington, DE (US)

( * ) Notice: Subject to any disclaimer, the term of this patent is extended or adjusted under 35 U.S.C. 154(b) by 190 days.

(21) Appl. No.: 10/625,418

(22) Filed: Jul. 23, 2003

(65) Prior Publication Data

US 2004/0220581 A1 Nov. 4, 2004

Related U.S. Application Data

(63) Continuation of application No. 09/692,980, filed on Oct. 20, 2000, now Pat. No. 6,599,291.

(51) Int. Cl.
*A61B 17/60* (2006.01)
(52) U.S. Cl. .......................................... 606/90; 606/84
(58) Field of Classification Search ................ 606/79, 606/90, 96, 99, 105, 86, 84; 623/17.11, 17.12, 623/17.13, 17.14, 17.15, 17.16
See application file for complete search history.

(56) References Cited

U.S. PATENT DOCUMENTS

| | | | |
|---|---|---|---|
| 3,486,505 A | 12/1969 | Morrison | |
| 3,848,601 A | 11/1974 | Ma et al. | |
| 4,059,115 A * | 11/1977 | Jumashev et al. | ............ 606/82 |
| 4,743,256 A | 5/1988 | Brantigan | |
| 5,423,825 A | 6/1995 | Levine | |
| 5,431,658 A | 7/1995 | Moskovich | |
| 5,484,437 A * | 1/1996 | Michelson | ................... 606/61 |
| 5,489,307 A | 2/1996 | Kuslich et al. | |
| 5,505,732 A | 4/1996 | Michelson | |
| 5,571,109 A | 11/1996 | Bertagnoli | |
| 5,700,264 A * | 12/1997 | Zucherman et al. | .......... 606/79 |
| 5,720,748 A | 2/1998 | Kuslich et al. | |
| 5,722,977 A | 3/1998 | Wilhelmy | |
| 5,772,661 A | 6/1998 | Michelson | |
| 5,904,686 A | 5/1999 | Zucherman et al. | |
| 6,004,326 A | 12/1999 | Castro et al. | |
| 6,042,582 A | 3/2000 | Ray | |

(Continued)

FOREIGN PATENT DOCUMENTS

EP 0 077 159 4/1983

(Continued)

*Primary Examiner*—Eduardo C. Robert
*Assistant Examiner*—Annette Reimers
(74) *Attorney, Agent, or Firm*—Krieg DeVault, LLP

(57) ABSTRACT

This invention relates to methods and instruments for performing a surgical procedure in a disc space between adjacent vertebrae. The instruments include a distractor and a cutting instrument. In one embodiment the distractor includes a body portion and a pair of flanges extending along opposite sides of the body portion such that a slot is formed between the flanges and the body portion. The cutting instrument is positionable over the body portion and into the slots of the distractor so that the flanges are positioned between the cutting instrument and the adjacent tissue.

20 Claims, 11 Drawing Sheets

U.S. PATENT DOCUMENTS

| | | |
|---|---|---|
| 6,045,579 A | 4/2000 | Hochshuler et al. |
| 6,083,225 A | 7/2000 | Winslow et al. |
| 6,126,664 A | 10/2000 | Troxell et al. |
| 6,190,414 B1 | 2/2001 | Young et al. |
| 6,197,033 B1 | 3/2001 | Haid, Jr. et al. |
| 6,224,607 B1 | 5/2001 | Michelson |
| 6,428,541 B1 * | 8/2002 | Boyd et al. .................... 606/61 |
| 6,599,291 B1 * | 7/2003 | Foley et al. ................... 606/79 |
| 6,641,582 B1 * | 11/2003 | Hanson et al. ................ 606/61 |
| 2002/0156481 A1 * | 10/2002 | Boyd et al. .................... 606/90 |

FOREIGN PATENT DOCUMENTS

| | | |
|---|---|---|
| WO | WO 98/17208 | 4/1998 |
| WO | WO 98/42269 | 10/1998 |
| WO | WO 99/52453 | 10/1999 |
| WO | WO 99/63891 | 12/1999 |
| WO | WO 00/42898 | 7/2000 |
| WO | WO 00/45709 | 8/2000 |

* cited by examiner

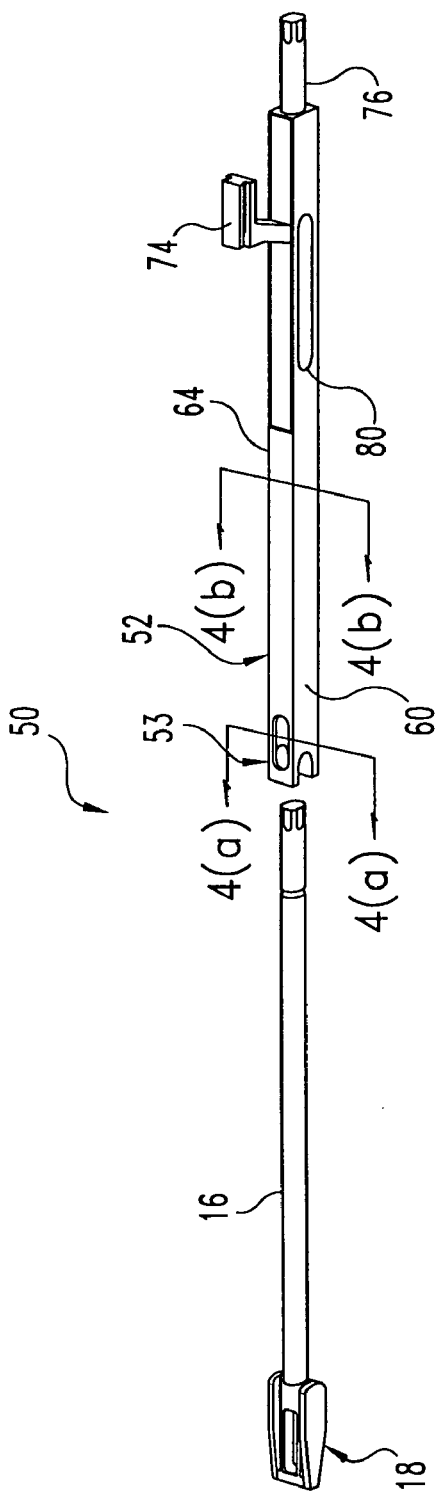

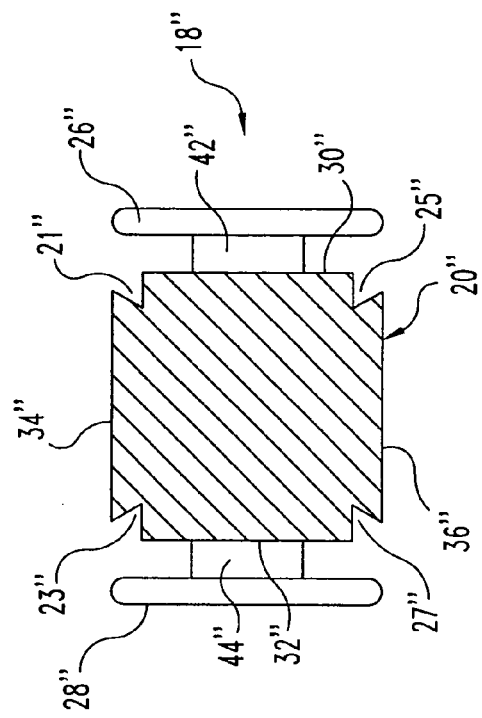
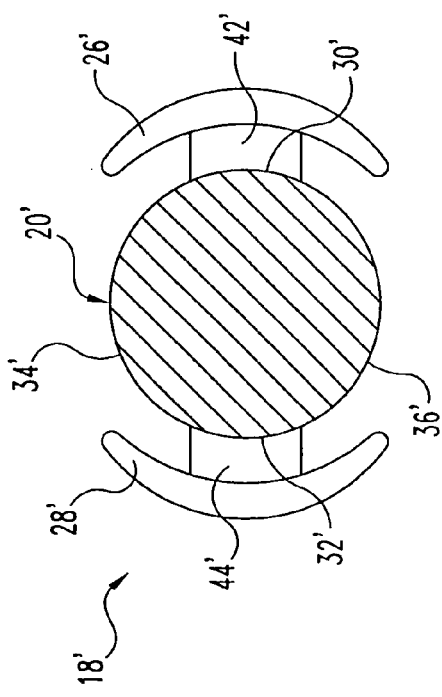

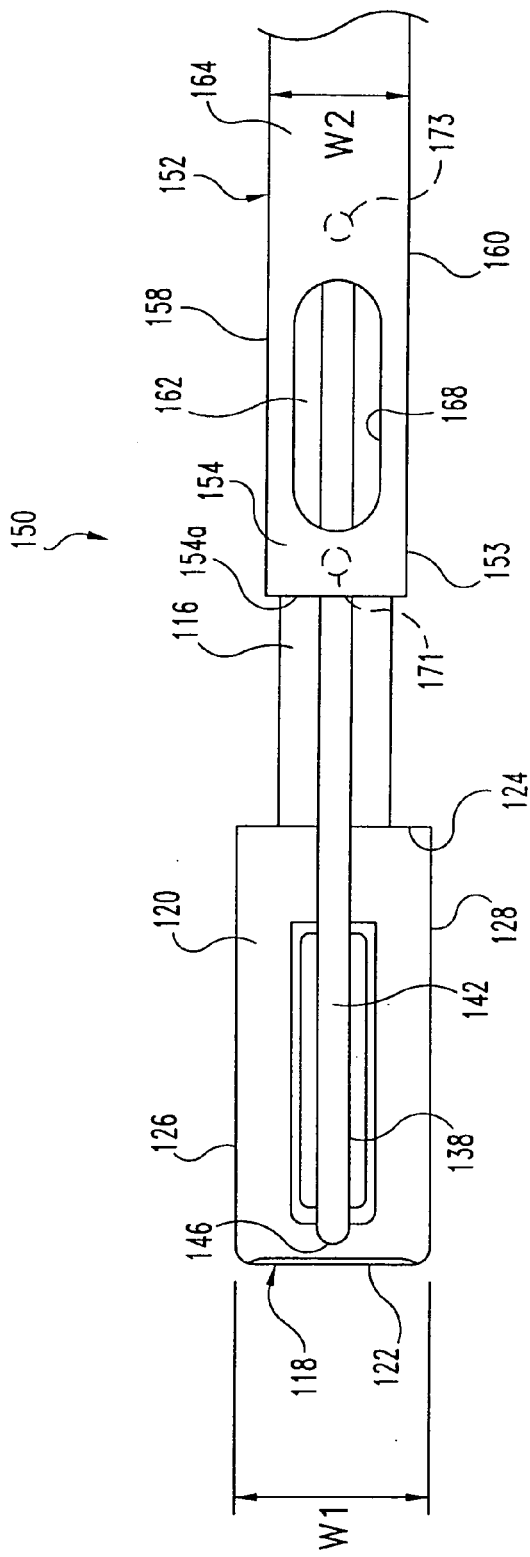
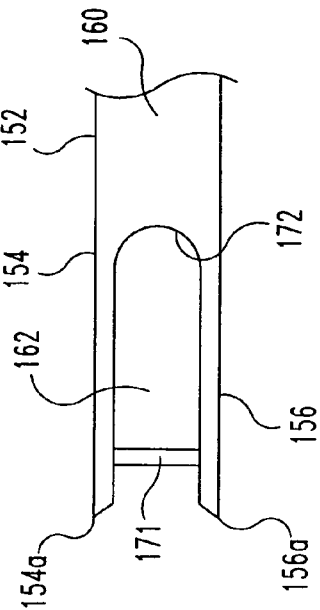
Fig. 12
Fig. 13

METHODS AND INSTRUMENTS FOR INTERBODY SURGICAL TECHNIQUES

CROSS-REFERENCE TO RELATED APPLICATION

This application is a continuation of U.S. patent application Ser. No. 09/692,980, filed Oct. 20, 2000, and issuing as U.S. Pat. No. 6,599,291 which is hereby incorporated by reference in its entirety.

FIELD OF THE INVENTION

The present invention relates to spinal surgical techniques and instruments. More particularly, while aspects of the present invention may have other applications, the invention provides instruments and techniques suited for interbody spinal surgery.

BACKGROUND OF THE INVENTION

Normally, intervertebral discs, which are located between endplates of adjacent vertebrae, stabilize the spine and distribute forces between the vertebrae and cushion vertebral bodies. The discs may be displaced or damaged due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility. Most typically surgical correction of a disc space includes a discectomy (surgical removal of a portion or the entire intervertebral disc.) The discectomy is often followed by preparation of the vertebral endplates to receive an implant, such as a fusion device. Fusion of the adjacent vertebrae is used to alleviate the pain associated with abnormal joint mechanics, premature development of arthritis, and damage to the spinal structures.

Traditional surgical procedures for correction of spinal defects can cause significant trauma to the nerves and vasculature adjacent the spine. The potential for tissue trauma can be of particular concern when the surgical procedure dictates the use of a cutting instrument in the disc space in order to remove disc and bone material to prepare the disc space for a fusion device, intervertebral spacer, or other implant. In order to minimize the potential trauma, surgical procedures can require denervation and devascularization of tissue adjacent the disc space. Other procedures require manipulation of the nerves and vasculature in order to provide clear access to the disc space. While reducing the potential for contact with surgical instruments, manipulation and removal of the nerves and vasculature can still result in trauma and an increase the time and difficulty of the surgical procedure.

U.S. Pat. No. 5,722,977 to Wilhelmy, incorporated herein by reference in its entirety, discloses a method and instrumentation for removal of a pair of rectangular blocks of vertebral bone tissue to provide an intervertebral recess. The instrumentation includes an intervertebral mortising cutter and a spacer that acts as a guide for the cutter. The procedure first requires the spacer to be inserted between the vertebral bodies. The cutter has a cutting head that defines a cavity that receives the spacer. In order to remove the bony material, the cutting head is pushed around the spacer and into the disc space. One disadvantage with the instrumentation disclosed in the '977 patent is that the cutting head is positioned between the spacer and the adjacent nerves and vasculature.

U.S. Pat. No. 5,484,437 to Michelson discloses a technique and associated instrumentation for inserting a fusion device from a posterior surgical approach that provides protection for the surrounding tissues and neurological structures during the procedure. As described in more detail in the '437 patent, the surgical technique involves the use of a distractor having a penetrating portion that urges the vertebral bodies apart to facilitate the introduction of the necessary surgical instrumentation. The '437 patent also discloses a hollow sleeve having teeth at one end that are driven into the vertebrae adjacent the disc space created by the distractor. These teeth engage the vertebra to maintain the disc space height during subsequent steps of the procedure following removal of the distractor. In accordance with one aspect of the '437 patent, a drill is passed through the hollow sleeve to remove portions of the disc material and vertebral bone to produce a prepared bore for insertion of the fusion device. One disadvantage with this technique is that the procedure is performed through a sleeve, thus limiting working space and visibility of the surgeon. A further disadvantage is that the height of the prepared disc space is limited by the spacing between penetrating portions of the distractor and the inner diameter of the sleeve.

While the more recent techniques and instrumentation represent an advance over earlier surgical procedures for the preparation of the disc space for insertion of implants between the vertebrae, the need for improvement still remains. The present invention is directed to this need for improvement and provides convenient methods and instruments for safe and effective spinal surgical procedures.

SUMMARY OF THE INVENTION

The present invention is directed to a spinal disc space distractor having a pair of flanges that protect adjacent tissue from a cutting instrument. The present invention is also directed to a spinal instrument assembly for distracting and cutting a disc space to prepare the disc space for insertion of one or more implants therein. The present invention is further directed to surgical methods and procedures using the distractor and spinal instrument assembly.

In accordance with one aspect of the invention, a distractor is provided. The distractor includes a body portion extending between a leading end and a trailing end. The body portion has an upper surface and an opposite lower surface, and opposite first and second sidewalls extending between the upper and lower surfaces. A first flange and a second flange extend from the leading end of the body portion towards its trailing end. The first and second flanges are spaced a distance from a respective one of the first and second sidewalls.

In accordance with a further aspect of the invention, a distractor is provided that includes a body portion extending between a leading end and a trailing end. The body portion has an upper surface and an opposite lower surface, and opposite first and second sidewalls extending between the upper and lower surfaces. The body portion includes a cavity formed therein that extends between the upper and lower surfaces.

In accordance with another aspect of the invention, a spinal instrument assembly for distracting and cutting the disc space between adjacent vertebrae is provided. The assembly includes a distractor and a cutter. The distractor includes a body portion extending between a leading end and a trailing end. The body portion includes opposite first and second sidewalls extending between the adjacent vertebral bodies. The distractor also includes a first flange and a second flange extending from the leading end towards the trailing end of the body portion. Each of the first and second flanges forms a slot along the body portion with a respective one of the first and second sidewalls. An elongated stem extends proximally from the trailing end of the body portion. The cutter includes a cutting head at the distal end of a shaft. An upper member, a lower member, and a pair of sidewalls extending therebetween form the shaft and cutting head. A channel extends through the cutting head and shaft. The channel is sized to receive the stem of distractor and to receive the body portion of the distractor such that the distal end of the sidewalls of the cutter are positionable in the slot and the body portion of the distractor is received in the channel.

According to a further aspect of the invention, a distractor is provided with an interfitting cutter having a channel sized to receive the distractor. The cutter has width that is less than the width of the distractor.

According to another aspect of the invention, a method for preparing a disc space between adjacent vertebrae is provided. The method includes: accessing the disc space through the skin and tissue of a patient; inserting a distractor into the disc space, the distractor having a body portion extending between a leading end and a trailing end, the distractor further including a first flange and a second flange extending from the leading end towards the trailing end of the body portion, each of the first and second flanges forming a slot along the body portion; and positioning a cutting head over the body portion and into the slots.

Further embodiments, forms, aspects, objects, features, benefits and advantages of the present invention shall become apparent from the detailed drawings and descriptions provided herein.

BRIEF DESCRIPTION OF THE DRAWINGS

FIG. 4 is a perspective view of a distractor-cutter assembly according to a further aspect of the present invention.

FIGS. 4(a) and 4(b) are sectional views taken through lines 4(a)–4(a) and 4(b)–4(b), respectively, of FIG. 4.

FIG. 6 is a cross-sectional view of an alternate embodiment distractor according to the present invention.

FIG. 7 is a cross-sectional view of another alternate embodiment distractor according to the present invention.

FIG. 12 is an enlarged top plan view of the distal end portion of another embodiment distractor and cutter according to the present invention.

FIG. 13 is a side elevational view of the distal end portion of the cutter of FIG. 12.

DETAILED DESCRIPTION OF THE PREFERRED EMBODIMENTS

Figure 1:
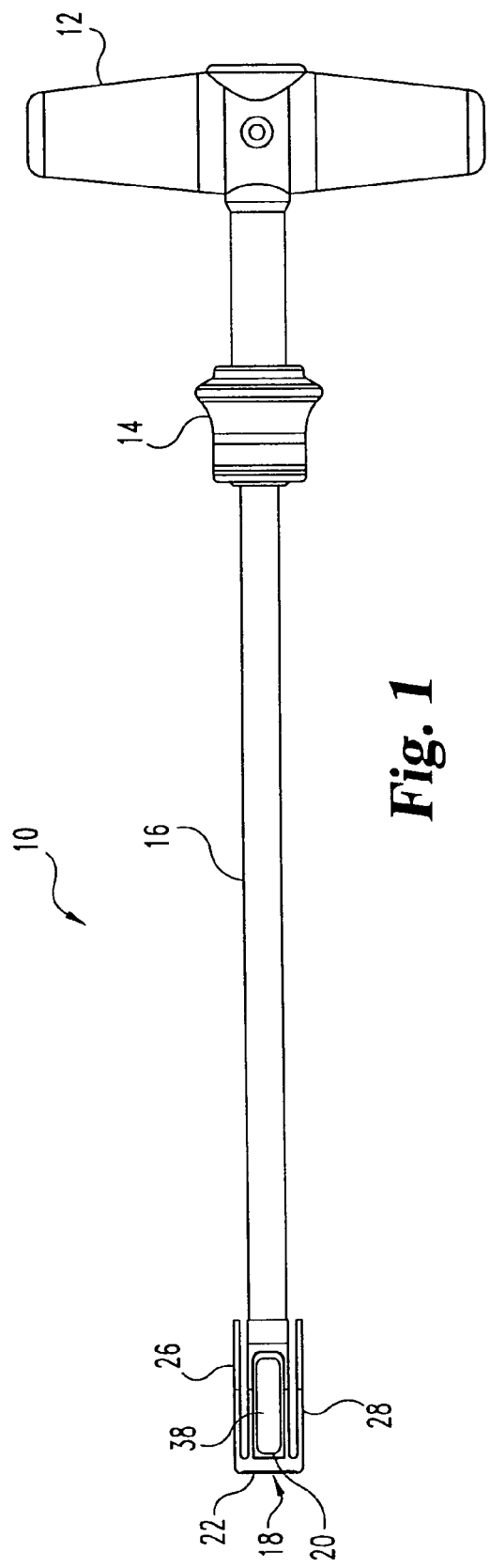
FIG. 1 is a top plan view of a distractor assembly according to one aspect of the present invention.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

The instruments and methods of the present invention have application to a wide range of surgical procedures, and particularly spinal procedures for preparing a disc space for insertion of an implant into the disc space. It is further contemplated that the surgical instruments and methods of the present invention have application in open surgical procedures and in minimally invasive surgical procedures.

Referring now to FIG. 1, a distractor assembly 10 insertable into the disc space between adjacent upper and lower vertebrae is provided. Distractor assembly 10 includes a handle 12 connected to a proximal end of a stem 16 via handle coupling 14. A distractor 18 is secured to a distal end of stem 16. It is contemplated that distractor 18 can be permanently affixed or removably attached to stem 16.

Figure 2:
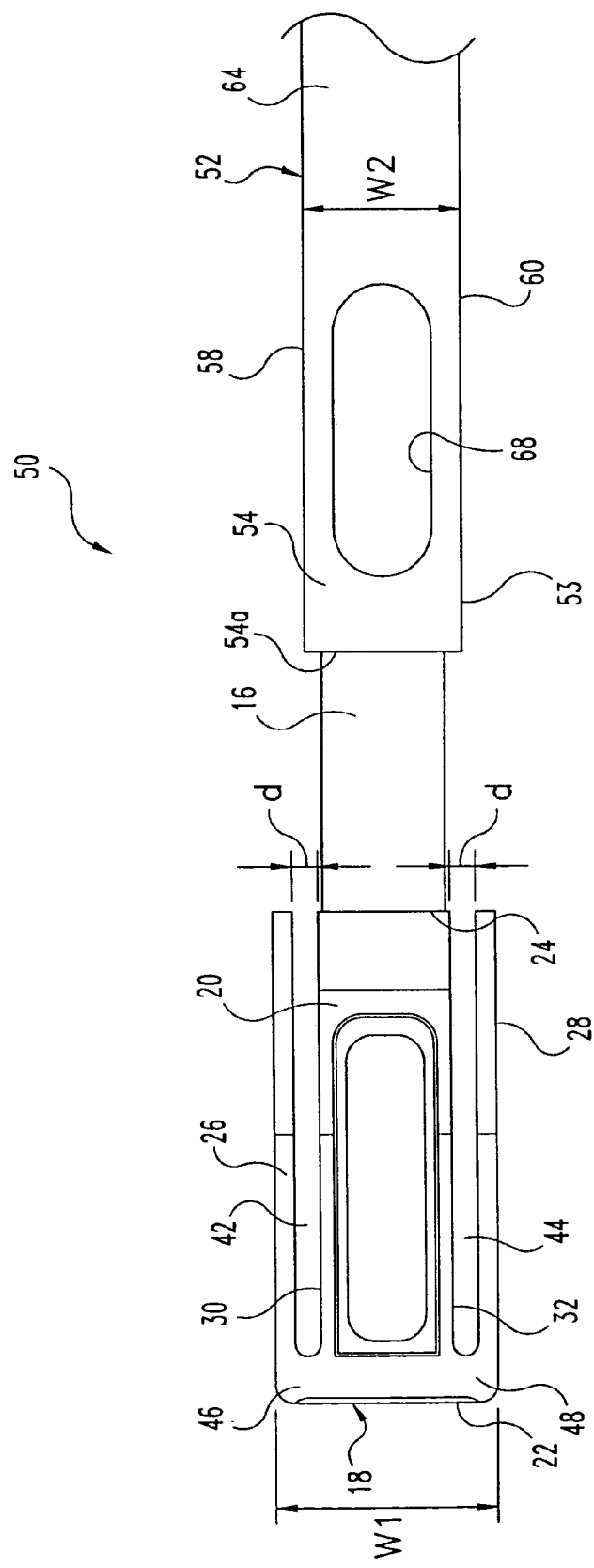
FIG. 2 is an enlarged top plan view of the distal end portion of the distractor assembly of FIG. 1 and the distal end portion of a cutter.

Referring now further to FIG. 2, distractor 18 includes a body portion 20 extending between leading end 22 and trailing end 24. Distractor 18 has a pair of opposite outermost sidewalls that are formed by a first flange 26 and a second flange 28 secured to body portion 20 at leading end 22. Flanges 26, 28 extend from leading end 22 towards trailing end 24. It is preferred that flanges 26, 28 are integrally formed with body portion 20 at leading end 22. In the illustrated embodiment, a first end wall 46 extends between leading end 22 and first flange 26 and a second end wall 48 extends between leading end 22 and second flange 28. However, flanges 26, 28 could also be removably attached to body portion 20.

Figure 3:
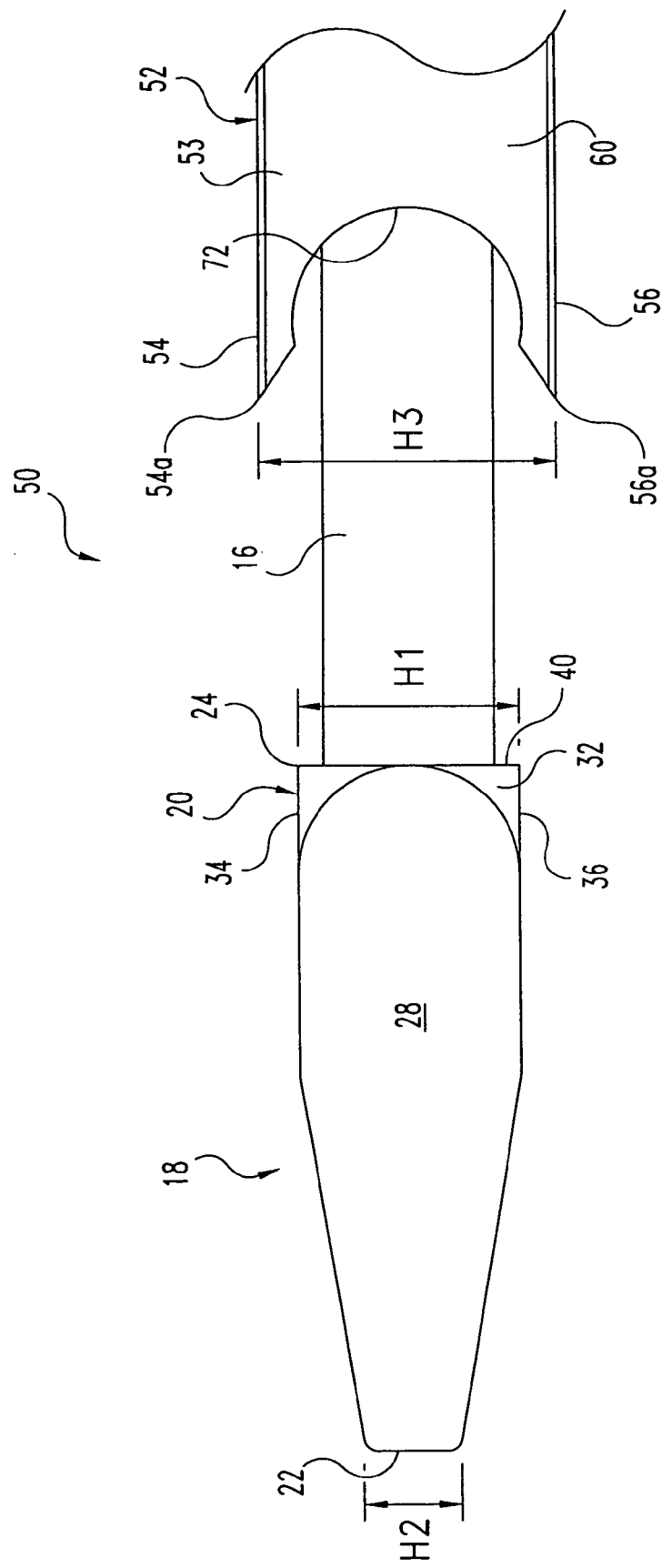
FIG. 3 is a side elevational view of the distal end portion of the distractor and cutter of FIG. 2.
Figure 5:
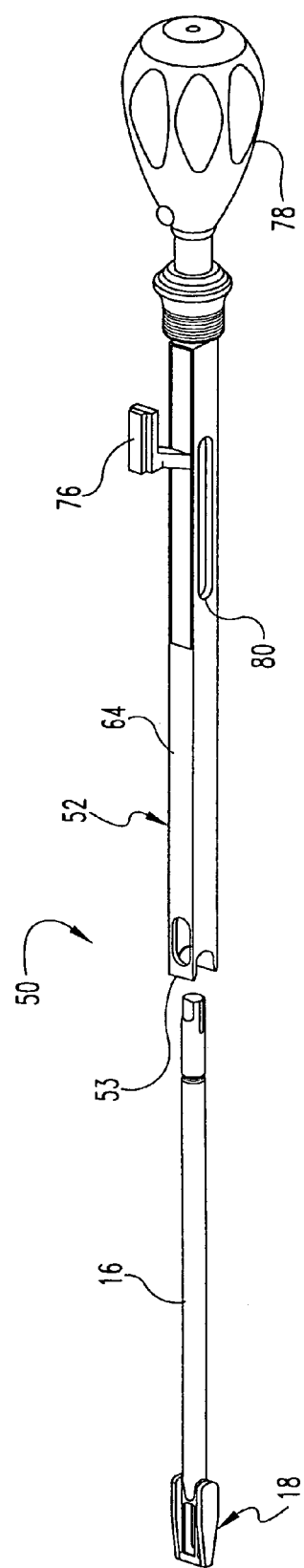
FIG. 5 is the perspective view of the distractor-cutter assembly of FIG. 4 with a handle attached the proximal end of the cutter.

Body portion 20 has first sidewall 30 and an opposite second sidewall 32. As shown in FIG. 3, each of the sidewalls 30, 32 extend towards the adjacent vertebrae between an upper surface 34 and a lower surface 36 of body portion 20. Referring back to FIG. 2, a first slot 42 is formed between first flange 26 and first sidewall 30. A second slot 44 is formed between second flange 28 and second sidewall 32. Slots 42 and 44 have a width "d" sized to accommodate the distal end of a cutting instrument 52, as discussed further below.

Body portion 20 further includes a cavity 38 formed therethrough extending between upper surface 34 and lower surface 36. Body portion 20 has a height H1 between upper surface 34 and lower surface 36 that corresponds to the desired height for the distracted disc space. In the illustrated embodiment, the leading end portion of body portion 20 tapers to a reduced height H2 between upper surface 34 and lower surface 36 at leading end 22 to facilitate insertion of distractor 18 into the disc space. Preferably, flanges 26, 28 have a height that is equal to or is less than height H1 of body portion 20, and have a tapered portion that corresponds to the taper of body portion 20 towards leading end 22. The depth of insertion of distractor 18 into the disc space can be monitored under direct vision, with a viewing element inserted in the disc space, or via x-ray or fluoroscopic imaging of distractor 18.

Referring to FIGS. 2–5, according to a further aspect of the invention a cutting instrument or cutter 52 is provided that cooperates with and is interfittable with distractor 18 to form a spinal instrument assembly 50. Spinal instrument assembly 50 provides for distraction of the adjacent vertebrae and for cutting material from the disc space and/or the adjacent vertebrae to form an implant insertion location. Cutter 52 includes a shaft 64 and a cutting head 53 at the distal end of shaft 64. Shaft 64 includes a first sidewall 58 and an opposite sidewall 60. Sidewalls 58 and 60 are connected by an upper member 54 and an opposite lower member 56. Upper member 54 includes an upper cutting edge 54a at its distal end and lower member 56 includes a lower cutting edge 56a at its distal end. While the illustrated embodiment has shaft 64 with a square cross-sectional shape, other shapes are also contemplated, including, for example, a circular or rectangular cross-section.

Shaft 64 includes an interior channel 62 formed therethrough that opens at the distal end of cutter 52. As shown in FIG. 4(a), channel 62 has a distal first portion 62a sized to receive stem 16 and body portion 20 of distractor assembly 10 with handle 12 removed from stem 16. Preferably, first portion 62a has a size slightly larger than body portion 20 and a shape approximating the shape of body portion 20. This provides a slip fit between body portion 20 and cutting head 53 that will guide cutting head 53 into the disc space and into the bony material of the adjacent vertebral bodies. Although the cross-section of the remaining proximal portion of channel 62 can have any shape, it is contemplated that the entire length of channel 62 has a shape that corresponds to the shape of first portion 62a.

Distractor 18 has an overall width W1 between the first flange 26 and second flange 28 that is greater the width W2 between the sidewalls 58, 60 of cutter 52. Distractor 18 thus ensures that when distractor 18 and cutter 52 are interfitted the flanges or outer-most sidewalls of distractor 18 are positioned adjacent the neural and vasculature tissue rather than the cutting edges of cutter 52.

In an alternate form shown in FIG. 4(b), channel 62 can be provided with a proximal second portion 62b that has a size slightly larger than stem 16 and a cross-sectional shape that approximates the outer surface of stem 16. This minimizes the relative movement between stem 16 and cutter 52 as cutter 52 is slidingly advanced along stem 16.

In one alternate embodiment shown in FIG. 6, distractor 18' has a body portion 20' with a circular cross-sectional shape defined by first sidewall 30', opposite second sidewall 32', upper surface 34' and lower surface 36'. First flange 26' and second flange 28' each have a curved shape that parallels body portion 20', although vertically oriented flanges could also be provided. First slot 42' is formed between first flange 26' and sidewall 30' and second slot 44' is formed between second flange 28' and sidewall 32'. In this embodiment, a cutter would be provided with a circular opening at its distal end and a cross-sectional shape that allows rotation, either manually or other known power means, about body portion 20' to cut the adjacent vertebral endplates. Flanges 26' and 28' protect the adjacent tissue from the rotating cutting head. Alternatively, a non-rotating cutter could be used with distractor 18'.

In another alternate embodiment shown in FIG. 7, distractor 18" has a first upper groove 21" formed between upper surface 34" and sidewall 30" and a second upper groove 23" formed between upper surface 34" and sidewall 32". Distractor 18" further has a first lower groove 25" formed between lower surface 36" and sidewall 30" and a second lower groove 27" formed between lower surface 36" and sidewall 32". The channel of cutter 52 can be configured to interfit with these grooves, thus allowing the grooves to guide the cutting edges of the cutter into the disc space. First slot 42" is formed between first flange 26" and sidewall 30", and second slot 44" is formed between second flange 28" and sidewall 32". Grooves 21", 23" 25", and 27" resist upward and downward movement of the cutting blades with respect to distractor 18" while flanges 26" and 28" protect the adjacent tissue from the cutting blade.

Referring back to FIGS. 2–5, upper member 54 includes an opening 68 and lower member 56 includes an opening 70 (FIG. 4(a)) identical to opening 68. These openings are substantially alignable with cavity 38 of distractor 18, and facilitate the removal of cut material from cavity 38 when the instrument assembly is withdrawn from the disc space after cutting bony material. Cutter sidewall 60 includes a recess 72 formed therein, and cutter sidewall 58 includes a similarly shaped recess (not shown.) The recesses allow cutting edges 54a and 56a to be advanced beyond the leading end 22 of distractor 18. End walls 46, 48 prevent cutting head 53 from being advanced too far beyond leading end 22 of body portion 20.

Sidewall 60 includes a window 80 to further provide visual observation and/or confirmation of the position of cutting head 53 with respect to distractor 18 by enabling viewing of depth markings on stem 16 of distractor assembly 10. Shaft 64 further includes an imaging probe 74 adjacent its proximal end to provide image-guided control and monitoring of cutter 52. Further details regarding probe 74 are provided in U.S. Pat. No. 6,021,343 to Foley et al., which is incorporated herein by reference in its entirety. Also contemplated are the use of x-ray and fluoroscopic imaging techniques to visualize cutting head 53 as it is inserted in the disc space.

Shaft 64 has a height H3 at its distal end that corresponds to the desired height of the prepared disc space into which the implant is to be inserted. It is contemplated that cutter 52 is inserted into the disc space with upper member 54 and lower member 56 parallel to the vertebral end plates and guided by body portion 20 of distractor 18. It is further contemplated that a number of cutters 52 of increasing height H3 may be provided and sequentially inserted over distractor 18 for removal of bony material from the vertebral endplates. While the illustrated cutter 52 has flat cutting edges 54a, 56a, other shapes for the cutting edges are also contemplated. For example, rounded upper and lower cutting edges could be used to cut an arched path in the vertebral endplates. A standard coupling 76 is provided at the proximal end of cutter 52 for attachment to a cutter handle 78 to facilitate gripping and control of cutter 52. The proximal end of cutter 52 can also be connected to or contacted by a driving tool, such as a slap hammer or the like to drive the cutting edges 54a, 56a into the bony material.

Figure 8:
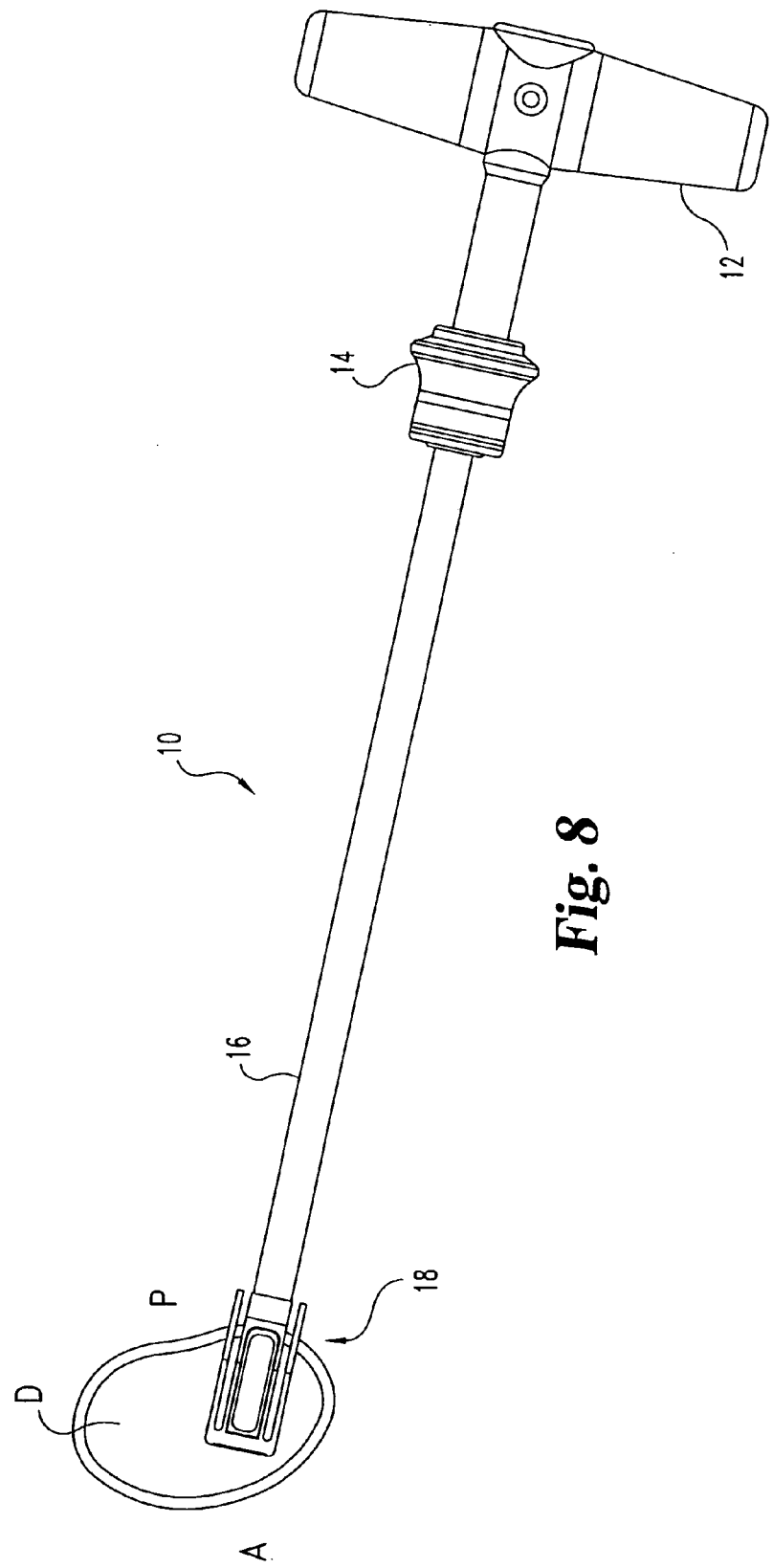
FIG. 8 is a top plan view of the distractor assembly of FIG. 1 with the distractor inserted into a disc space from a generally posterior approach.

The steps of the spinal surgical procedure in accordance with one aspect of the present invention are depicted in FIGS. 8–11. In the depicted steps, there is illustrated a disc space D between adjacent vertebral bodies having a posterior side P and an anterior side A. The skin and tissue are excised and disc space D is accessed using any known surgical technique and instruments. Typically, an opening is made in the disc annulus at the desired entry location, and all or part of the disc nucleus can be excised through this annulus opening. As shown in FIG. 8, distractor 18 of distractor assembly 10 is inserted into disc space D to distract disc space to the desired height between the adjacent vertebrae. It is contemplated that, if necessary, the disc space can be sequentially distracted by known distractor instruments before insertion of distractor 18 or sequentially distracted by a number of distractors 18 of increasing height H1 until the desired disc space height is obtained.

Figure 9:
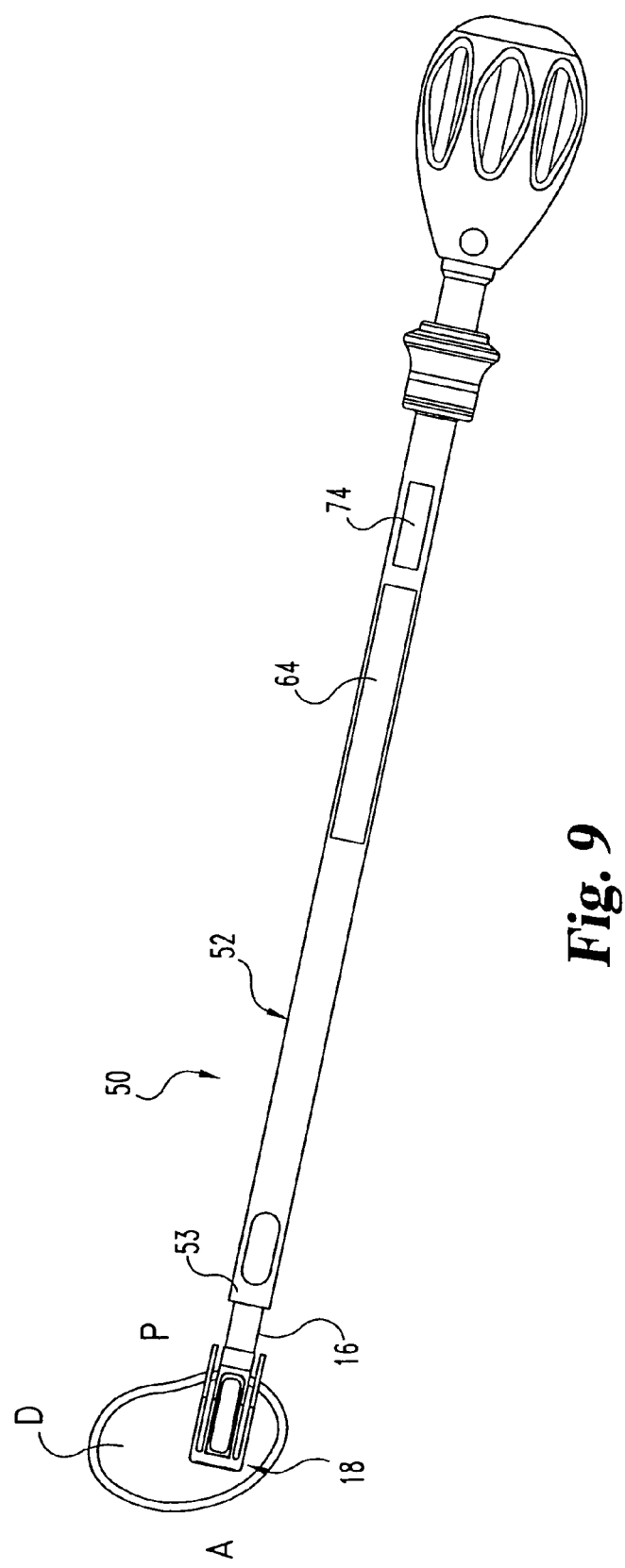
FIG. 9 is a top plan view of the distractor-cutter assembly of FIG. 5 with the distractor in the disc space and the cutter adjacent the disc space.
Figure 10:
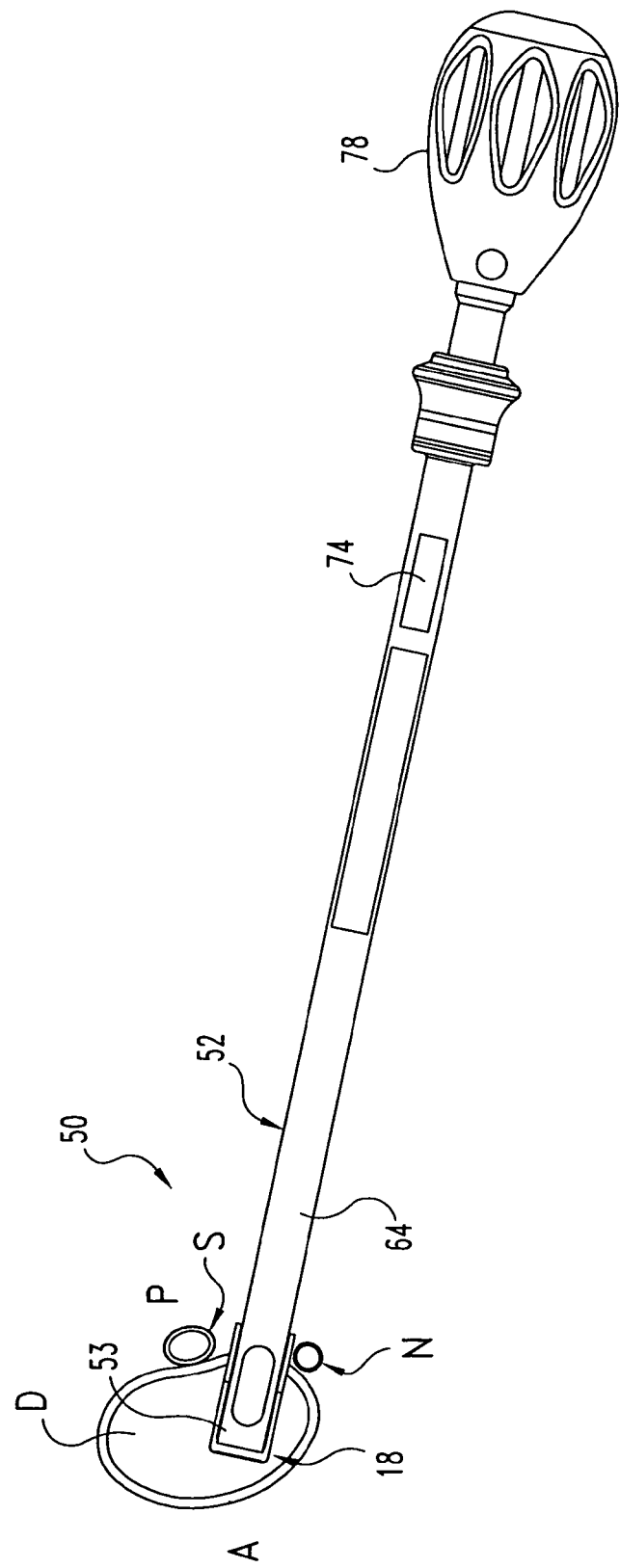
FIG. 10 is the distractor-cutter assembly of FIG. 5 with the distractor and the cutter in the disc space.
Figure 11:
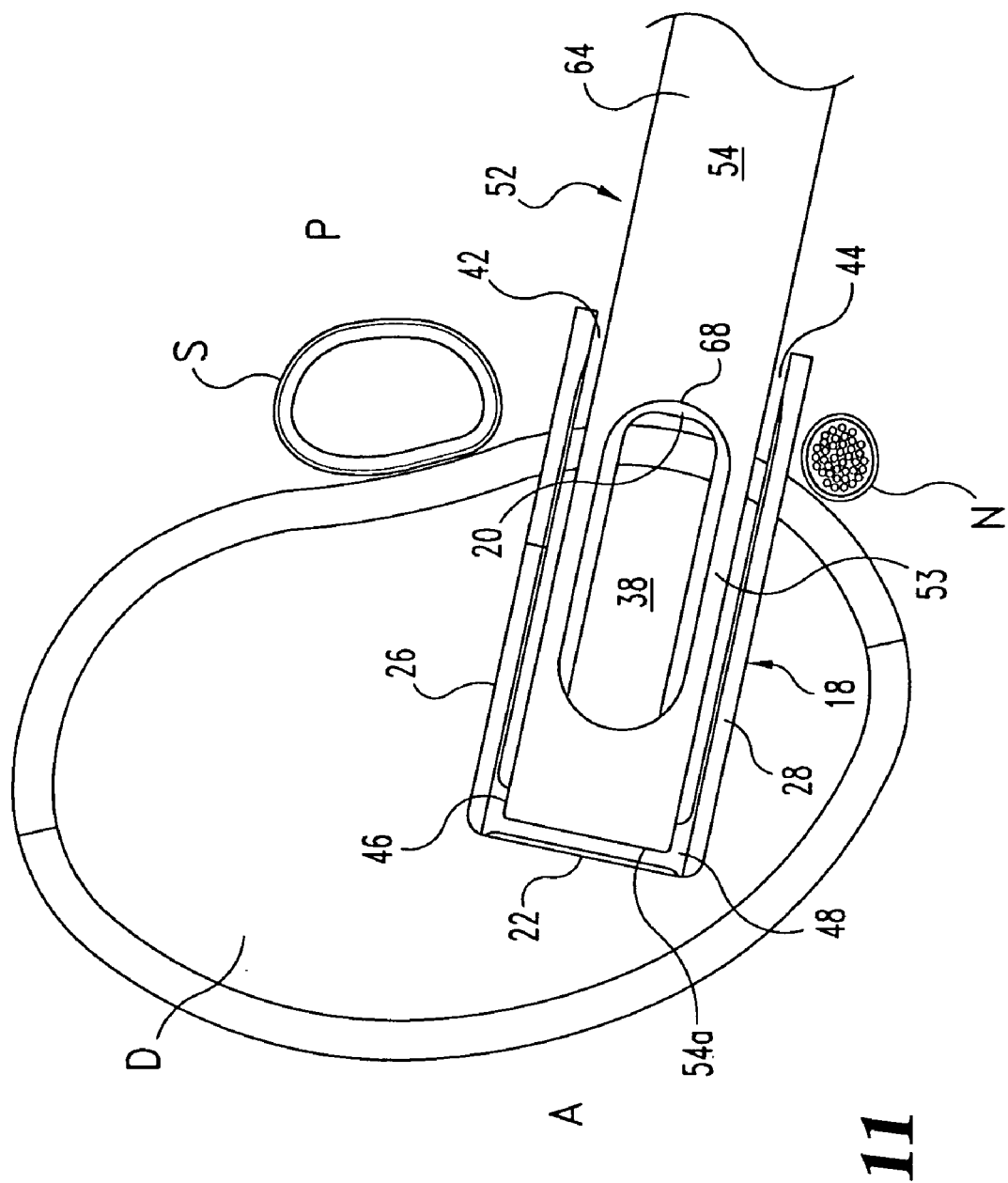
FIG. 11 is an enlarged view of the distal end portion of the distractor and cutter in the disc space.

When the desired distraction has been achieved, handle 12 is then removed from the proximal end of stem 16 and, as shown in FIG. 9, cutter 52 is slid over the proximal end of stem 16 to position cutting head 53 adjacent the disc space and distractor 18. As shown in FIGS. 10 and 11, cutter 52 is advanced over body portion 20 of distractor 18 so that the bony material of the vertebral endplates is cut by cutting edges 54*a* and 56*a*. At least a portion of the cut material is deposited in cavity 38 of distractor 18. Cutter 52 forms a path or track for implant insertion while distractor 18 maintains disc space distraction. Flanges 26, 28 protect the adjacent vasculature and nerves, such as dura S and nerve root N, as cutter 52 is advanced over and interfitted with body portion 20.

When the implant insertion path is cut to the desired depth into the vertebral endplates, distractor assembly 10 and cutter 52 can be removed from disc space D. The material in cavity 38 can be removed through openings 68, 70 of cutter 52 to facilitate disassembly of the instruments. Further cleaning and debris removal in disc space D can be completed if necessary before one or more implants are inserted into the disc space. The inserted implant may be any device suitable for insertion into the disc space. In one specific form, it is contemplated that an implant is inserted in the disc space in order to restore the disc height, restore segmental alignment and balance, and immobilize the unstable degenerated intervertebral disc area. The implant(s) may be conveniently implanted with any known instruments and tools, and any instrument that will firmly hold the implant and permit insertion in the disc space is contemplated. In one specific form, the implant is a fusion device such as a bone dowel, push-in implant, threaded implant or the like, that is advanced into the site prepared with the instruments of the present invention at the subject disc space. The inserted implant provides support of the adjacent vertebrae, and can be packed with bone growth material to facilitate fusion. Graft material may also be placed directly in the prepared bore in the disc space, either without any implant or packed around the inserted implant.

It is also contemplated that more than one implant can be inserted at bi-lateral locations in the disc space through either a single lateral or transforaminal approach to the disc space, or through multiple approaches taken with an anterior or posterior mid-line approach to the disc space. The inserted implants provide bilateral support of the adjacent vertebrae, and can be packed with bone growth material to facilitate fusion.

The instruments and methods have been disclosed with reference to a particular application for disc space preparation and implant insertion from an oblique, posterior approach to the spine. However, it will be understood that the instruments and methods may be utilized, or modified for use, for a variety of surgical applications and approaches including, but not limited to, a unilateral posterior approach, a lateral approach, other oblique approaches, and an anterior approach. The instruments also have applications with laparoscopic or endoscopic procedures on the spine, such as, through the working channel cannula/endoscope decribed in U.S. patent application No. application Ser. No. 09/160,882 filed Sep. 15, 1998, which is incorporated herein by reference in its entirety.

Referring now further to FIGS. 12–13, an alternate embodiment spinal instrument assembly having a cutter guided by a distractor will be described. Assembly 150 includes a distractor 118 having a body portion 120 extending between leading end 122 and trailing end 124. Body 120 is attached to stem 116 at trailing end 124. Distractor 118 has a pair of opposite outermost sidewalls 126, 128 formed by body portion 120. In one form, a slot 142 extends from position adjacent leading end 122 proximally through body portion 120 and stem 116. Slot 142 preferably extends substantially along the longitudinal center axis of distractor 118. An end wall 146 is formed between leading end 122 and slot 142.

Body portion 120 further includes a cavity 138 formed therethrough extending between the upper and lower surfaces of body portion 120. Body portion has a height between the upper and lower surface that corresponds to the desired height for the distracted disc space. The leading end portion of body portion 120 can be tapered as discussed above with respect to distractor 18.

A cutting instrument or cutter 152 is provided that cooperates and interfits with distractor 118 to form spinal instrument assembly 150. Cutter 152 includes a shaft 164 and a cutting head 153 at the distal end of shaft 164. Shaft 164 includes a first sidewall 158 and an opposite sidewall 160. Sidewalls 158 and 160 are connected by an upper member 154 and an opposite lower member 156. Upper member 154 includes an upper cutting edge 154*a* at its distal end and lower member 156 includes a lower cutting edge 156*a* at its distal end. Upper member 154 includes an opening 168 and lower member 156 includes an opening (not shown) that are substantially alignable with cavity 138 of distractor 118, and facilitate the removal of cut material from cavity 138. Cutter sidewall 160 includes a recess 172 formed therein, and cutter sidewall 158 includes a similarly shaped recess (not shown.)

Shaft 164 includes an interior channel 162 formed therethrough that opens at the distal end of cutter 152. Channel 162 is sized to receive stem 116 and body portion 120 of distractor 118. This provides a slip fit between body portion 120 and cutting head 153 that will guide cutting head 153 into the disc space and into the bony material of the adjacent vertebral bodies. The sidewall recesses are sized and shaped to receive body portion 120 of distractor 118 and allow cutting edges 154*a* and 156*a* to be advanced beyond the leading end 122 of distractor 118. End wall 146 prevents cutting head 153 from being advanced too far beyond leading end 122.

Where a slot 142 is provided in distractor 118, a first guide pin 171 and a second guide pin 173 are positioned in channel 162. Guide pins 171, 173 extend between and are secured to upper member 154 and lower member 156. Guide pins 171, 173 are slidingly received in guide slot 142. Cutter 152 can be advanced over body portion 120 with body portion 120 positioned in channel 162 and received in and extending laterally outwardly from sidewall recesses 172. Guide pins 171, 173 positioned in guide slot 142 prevent lateral deviation of cutting head 153 with respect to body portion 120 as cutter 152 is advanced over distractor 118. Pins 171, 173 further act as braces that stabilize and strengthen shaft 164 in the area of the sidewall recesses.

Distractor 118 has an overall width W1 between the first sidewall 126 and second sidewall 128 that is greater the width W2 between the sidewalls 158, 160 of cutter 152. Guide slot 142 and pins 171, 173 and the interfitted arrangement between distractor 118 and cutter 152 ensure that the sidewalls of distractor 118 are positioned adjacent to the neural and vasculature tissue rather than the cutting edges of cutter 152.

While the invention has been illustrated and described in detail in the drawings and the foregoing description, the same is considered to be illustrative and not restrictive in character. It is understood that only the preferred embodiments have been shown and described and that all changes and modifications that come within the spirit of the invention are desired to be protected.

What is claimed is:

1. A method for preparing a spinal disc space, comprising:
inserting a body portion of a distractor into the spinal disc space with an upper surface of the body portion adjacent an endplate of an upper vertebra and a lower surface of the body portion adjacent an endplate of a lower vertebra, wherein the body portion includes at least one flange extending from a distal end of the body portion towards a proximal end of the body portion;
advancing a cutting instrument over the body portion between the at least one flange and the body portion to remove material between at least one of the upper and lower surfaces of the body portion and the adjacent vertebra; and
depositing cut material into a cavity formed in the body portion, the cavity opening toward at least one of the upper and lower surfaces.

2. The method of claim 1, wherein the cavity opens at each of the upper and lower surfaces.

3. The method of claim 2, further comprising advancing the cutting instrument over the body portion to remove material between the upper and lower surfaces of the body portion and each of the adjacent vertebra.

4. The method of claim 3, further comprising depositing cut material into the cavity through each of the openings of the body portion.

5. The method of claim 1, wherein advancing the cutting instrument includes contacting the distal end of the body portion to limit advancement of the cutting instrument into the disc space.

6. The method of claim 1, wherein inserting the body portion includes contacting the endplate of the upper and lower vertebrae with the adjacent one of the upper and lower surfaces of the body portion.

7. The method of claim 1, further comprising:
removing the cutting instrument and the body portion from the disc space; and
inserting an implant in the spinal disc space.

8. The method of claim 1, wherein the body portion includes a second flange opposite the at least one flange, the second flange extending from the distal end towards the proximal end of the body portion; and
advancing the cutting instrument includes advancing the cutting instrument over the body portion between the body portion and each of the flanges.

9. The method of claim 1, wherein advancing the cutting instrument includes navigating the cutting instrument with image guidance.

10. A method for preparing a spinal disc space, comprising:
inserting a body portion of a distractor into the spinal disc space;
advancing a cutting instrument over the body portion into the spinal disc space; and
limiting advancement of the cutting instrument into the spinal disc space by contacting the cutting instrument with a distal end wall of the body portion, wherein advancing the cutting instrument includes advancing the cutting instrument between a first flange and a second flange of the distractor, each of the first and second flanges extending from a distal end of the body portion toward a proximal end of the body portion, each of the first and second flanges forming a slot along the body portion for receiving the cutting instrument.

11. The method of claim 10, wherein:
the distal end wall includes a first width; and
the cutting instrument includes an elongated shaft having a distal cutting end, the distal cutting end of the shaft configured to interfit with the body portion and includes a distally opening channel to receive the body portion of the distractor, the distal cutting end including a second width that is less than the first width.

12. The method of claim 10, further comprising depositing cut material into a cavity formed in the body portion, the cavity opening toward at least one of upper and lower surfaces of the body portion.

13. The method of claim 10, further comprising:
removing the cutting instrument and the body portion from the disc space; and
inserting an implant in the spinal disc space.

14. The method of claim 10, wherein inserting the body portion includes contacting endplates of vertebrae adjacent the spinal disc space with an adjacent one of an upper surface and a lower surface of the body portion.

15. A method for preparing a spinal disc space, comprising:
inserting a body portion of a distractor into the spinal disc space;
advancing a cutting instrument over the body portion into the spinal disc space; and
limiting advancement of the cutting instrument into the spinal disc space by contacting the cutting instrument with a distal end wall of the body portion, wherein advancing the cutting instrument includes advancing the cutting instrument between at least one flange of the distractor and the body portion of the distractor, the at least one flange extending from a distal end of the body portion towards a proximal end of the body portion and forming a slot along the body portion for receiving the cutting instrument.

16. The method of claim 15, wherein:
the distal end wall includes a first width; and
the cutting instrument includes an elongated shaft having a distal cutting end, the distal cutting end of the shaft configured to interfit with the body portion and includes a distally opening channel to receive the body portion of the distractor, the distal cutting end including a second width that is less than the first width.

17. The method of claim 15, wherein advancing the cutting instrument includes advancing the cutting instrument between a first flange and a second flange of the distractor, each of the first and second flanges extending from the distal end of the body portion toward the proximal end of the body portion, each of the first and second flanges forming a slot along the body portion for receiving the cutting instrument.

18. The method of claim 15, further comprising:
removing the cutting instrument and the body portion from the disc space; and
inserting an implant in the spinal disc space.

19. The method of claim 15, wherein inserting the body portion includes contacting endplates of vertebrae adjacent the spinal disc space with an adjacent one of an upper surface and a lower surface of the body portion.

20. The method of claim 15, further comprising depositing cut material into a cavity formed in the body portion, the cavity opening toward at least one of upper and lower surfaces of the body portion.

* * * * *